United States Patent [19]

Sleytr et al.

[11] Patent Number: 5,043,158
[45] Date of Patent: Aug. 27, 1991

[54] IMMUNOGENIC COMPOSITIONS CONTAINING ORDERED CARRIERS

[75] Inventors: Uwe B. Sleytr; Wolfgang Mundt; Paul Messner, all of Vienna, Austria; Richard H. Smith; Frank M. Unger, both of Edmonton, Canada

[73] Assignee: Chembiomed, Ltd., Edmonton, Canada

[21] Appl. No.: 487,729

[22] Filed: Mar. 2, 1990

Related U.S. Application Data

[63] Continuation-in-part of Ser. No. 233,674, Aug. 18, 1988, abandoned.

[30] Foreign Application Priority Data

Aug. 21, 1987 [DE] Fed. Rep. of Germany ....... 3717897
Aug. 22, 1988 [CA] Canada ................................. 575340

[51] Int. Cl.$^5$ ..................... A61K 39/385; C07K 17/02
[52] U.S. Cl. ......................................... 424/92; 424/88; 514/8; 530/395; 530/403; 530/404; 530/405; 530/406; 530/810
[58] Field of Search ............... 530/395, 403, 404, 405, 530/406, 810; 424/88, 92; 514/8

[56] References Cited

U.S. PATENT DOCUMENTS

| | | | |
|---|---|---|---|
| 4,578,269 | 3/1986 | Morein | 424/88 |
| 4,801,578 | 1/1989 | Monsigny et al. | 514/8 |
| 4,837,171 | 6/1989 | Codington | 436/548 |

FOREIGN PATENT DOCUMENTS

| | | |
|---|---|---|
| 0037388 | 10/1981 | European Pat. Off. . |
| 0060422 | 9/1982 | European Pat. Off. . |
| 0118831 | 9/1984 | European Pat. Off. . |
| 0180564 | 5/1986 | European Pat. Off. . |
| 0198388 | 6/1986 | European Pat. Off. . |
| 0191536 | 8/1986 | European Pat. Off. . |

OTHER PUBLICATIONS

Lovgren et al., (1987) J. Immunol. Methods, 98:137–143.
Gray (1978) Methods Enzymol., 50:155–160.
Warren et al., Ann. Rev. Immunol. (1986) 4:369–388.
Bellstedt et al., J. Immunol. Meth. (1987) 98:249–255.
Livingston et al., J. Immunol. (1987) 138(5):1524–1529.
Avrameas et al., Scand. J. Immunol. (1978) 8:7–23.
Makela et al., Scand. J. Immunol. (1984) 19:541–550.
Seizen et al., FEBS Letters (1979) 100(1):75–80.

Primary Examiner—Jeffrey E. Russel
Assistant Examiner—Kay Kim
Attorney, Agent, or Firm—Irell & Manella

[57] ABSTRACT

Superior pharmaceutical compositions which comprise carriers coupled to epitope-bearing moieties are described. The carriers are crystalline or paracrystalline glycoproteins, especially those derived from S-layers of microbial cell walls. These conjugates are capable of eliciting the formation of antibodies as well as a T-cell response.

6 Claims, 7 Drawing Sheets

Fig. 1

• · · · · • bovine serum albumin, standard o———o bovine serum albumin attached to unoxidized S-layers (unspecific adsorption)

◇ · · · ◇ bovine serum albumin bound to oxidized S-layers (formation of Schiff's bases involving $\epsilon$ - amino groups of lysine residues)

IMMUNOGENIC COMPOSITIONS CONTAINING ORDERED CARRIERS

CROSS-REFERENCE TO RELATED APPLICATION

This application is a continuation-in-part of U.S. Ser. No. 233,674, filed Aug. 18, 1988 and now abandoned.

FIELD OF THE INVENTION

The invention relates to improved immunogenic compositions in which haptens to which an immune response is desired are conjugated to a crystalline or paracrystalline carriers, especially those represented by bacterial surface layers, or "S-layers."

BACKGROUND ART

When an immune response is desired to a particular antigen or hapten, it may be necessary to supplement the administration of the hapten with a material which enhances its ability to elicit either or both a B-cell mediated or T-cell mediated response. One general class of such supplementing agents has generally been classified as adjuvants. These are materials administered along with the hapten which seem to aid in securing the desired response. The use of killed bacteria and the products thereof as such adjuvants has a considerable history, and the use of Freund's Complete Adjuvant (killed Mycobacteria) or other bacteria and their components such as peptidoglycan as immunomodulators has been reviewed, for example, by Warren, H. S., et al., *Ann Rev Immunol* (1986) 4:369. Naked or acid-treated bacteria have also been shown to act as adjuvants to induce humoral immunity to carbohydrate moieties on large glycoproteins by Bellstedt, D. U., et al., *J Immunol Meth* (1987) 98:249–255; Livingston, P. O., et al., *J Immunol* (1987) 138:1524–1529.

European patent application publication No. 180,564 describes the preparation of a complex from bacterial substrates designated "Iscom." This complex is prepared by solubilizing the hydrophobic peptides from bacteria into detergent, removing the detergent from the solubilized material and replacing it with glycosides, such as saponin.

Haptens which are contained in small molecules, especially carbohydrates, are also rendered more immunogenic by conjugation to a carrier such as bovine serum albumin, keyhole limpet hemocyanin, diphtheria or tetanus toxoids and the like. The resulting conjugate vaccination antigens possess increased immunogenic potential with respect to the low-molecular weight haptens.

Finally, the immune response to weak immunogens, such as carbohydrate antigens, is usually an antibody response, mediated by B-lymphocytes, whereas effective protection through vaccination would generally require participation of T-lymphocytes in the immune response. To modulate the immune response to carbohydrate haptens in favor of T-lymphocyte-mediated immunity, is another reason why B-lymphocyte-dependent haptens have been attached to protein carriers.

Depending on the nature of chemical linking process chosen, such binding of haptens to carriers is often poorly defined and poorly reproducible. Also, where the carriers are toxoids such as diphtheria or tetanus toxoids, their formation from the corresponding toxins is sometimes incomplete so that toxoid preparations show residual toxic activity.

The invention provides two-dimensional crystalline carriers which permit definition of these parameters so that an ordered structure bearing the immunostimulatory or immunoregulatory substance can be obtained, and problems associated with toxicity are minimized.

DISCLOSURE OF THE INVENTION

In accord with the present invention, the problems of low or lacking immunogenicity, lack of T-lymphocyte-mediated response, ill-defined (poorly reproducible) coupling of haptens or immunoactive substances, and residual toxicity of antigen carriers is solved by using as the carrier to which the immunoactive substances are bound two-dimensional crystalline arrays of proteins or glycoproteins.

These aggregates may also be covalently cross-linked. By virtue of the crystalline structure of the two-dimensional arrays, the carrier molecules display a constant, precisely defined spatial orientation with respect to each other; thus both the nature of the linkages and the number and spatial orientation of the bound haptens or immunoactive substances and the distance between the binding sites which can carry the haptens or immunoactive substances are always precisely defined.

Furthermore, by the practice of this invention it is possible to choose carriers structured so that they, by virtue of their shape, size, arrangement and surface properties, are preferentially taken up by immunologically active accessory cells. Such uptake by accessory cells, e.g., macrophages, dendritic cells or Langerhans cells permits a more efficient immune response to be achieved through enhanced processing and presentation of the desired hapten.

Thus, in one aspect, the invention is directed to pharmaceutical compositions comprising a two-dimensional crystalline carrier coupled to a moiety which bears an epitope, e.g., a hapten, to which an immunological response is desired. The two-dimensional crystalline array may optionally be stabilized by covalent cross-linking. A particularly preferred crystalline carrier is obtained from isolation of the S-layers of microbial cell walls.

In another aspect, the invention is directed to methods to prepare the pharmaceutical compositions of the invention which comprises coupling the epitope-bearing moieties to the above carriers. In still another aspect, the method is directed to methods to elicit a T-cell mediated or B-cell mediated immune response to an epitope of interest, which method comprises administration of the compositions of the invention to a vertebrate subject in an amount effective to elicit the desired response.

MODES OF CARRYING OUT THE INVENTION

The invention provides pharmaceutical compositions which are capable of enhancing the immune response by virtue of employing carriers which are two-dimensional crystalline arrays. Various methods of attaching the imminoactive substances to these carriers may also be employed. The resulting compositions may be used both for stimulation of B-cell and T-cell responses.

NATURE OF THE CARRIERS AND COMPOSITIONS

Advantageously, the two-dimensional crystalline arrays may consist of glycoproteins or proteins whereby the structure of the carriers may further approximate the shape of a bacterium. The appropriate arrays may be derived from one or several microbial cell wall layers. Thus, the proteins or glycoproteins composing thse arrays are obtained in an especially simple manner. Such suitable arrays may contain other adhering cell wall components. In certain cases, microbial cell wall fragments as such can be used to carry the immunoactive substances. Particularly suitable as sources of this type of carrier are those microorganisms which, aside from the crystalline surface layer proteins, contain additional rigid layers such as those composed of peptidoglycan or pseudo-murein.

Figure 1:
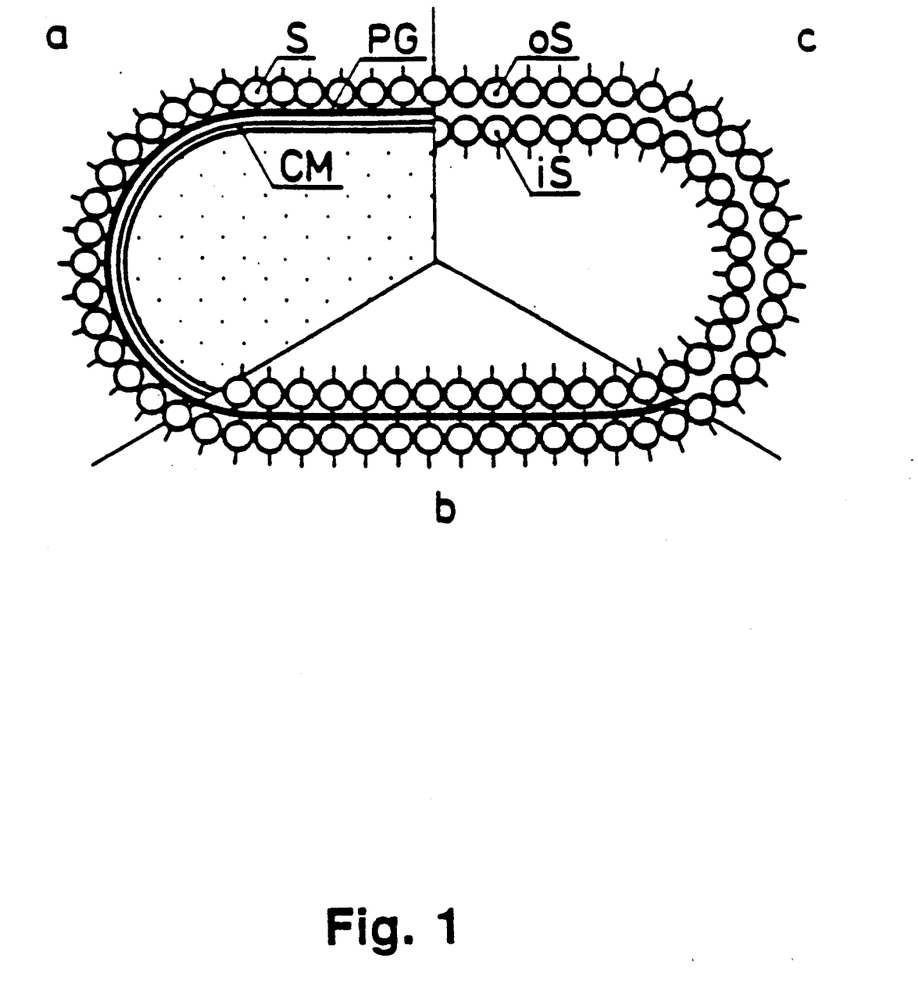
FIG. 1 is an illustration which shows the three stages of purification of S-layers from intact bacteria.

FIG. 1 shows several stages of purification of typical bacterial cell wall arrangements. Section a shows a section of intact bacterial cell wall wherein S represents the S-layer; PG represents peptidoglycan and CM represents the cytoplasmic membrane. As shown, the S-layer is associated with the proteoglycan and cytoplasmic membrane in a layered structure.

Section b shows the empty peptidoglycan sacculus after glutaraldehyde fixation. The cytoplasmic membrane is removed, and the fixed segment contains a double S-layer separated by the peptidoglycan.

Section c shows the glutaraldehyde fixed S-layer composition after lysozyme treatment to remove the peptidoglycan. The designations iS and oS represent the inner and outer S-layers.

In a preferred embodiment of the present invention, the two-dimensional crystalline arrays are derived from microbial cell walls as S-layers with or without additional peptidoglycan layers. In order to prepare these aggregates, bacteria are incubated with detergent at elevated temperatures of 30°–60° C., preferably around 50° C., for a suitable time period to disintegrate the cytoplasm and plasma membrane of the organism. Suitable detergents include, for example Triton X-100, various alkylpolyoxyethylene ethers, various acylpolyoxyethylene sorbitol esters, such as the Tweens, and the like. Intact bacteria may be treated with the detergent, or the culture may be sonicated or otherwise disrupted in the presence of buffer when the cellular shape of the microorganism does not need to be conserved. The nonsolubilized components are recovered, preferably through centrifugation, and the pellets are washed. It is desirable to further remove cytoplasmic components and nucleic acids by treatment with suitable enzymes including DNAse, RNAse, and the like. The washed and pelleted aggregates containing the S-layers are then utilized as carriers, preferably after treatment with a cross-linking agent such as glutaraldehyde. The cross-linker is added in an amount which stabilizes the ordered structure of the S-layer.

Also, optionally, the residual peptidoglycan can be removed from the recovered S-layers by treatment with a peptidoglycan-degrading enzyme, for example lysozyme. The recovered pellet is treated with the enzyme at about 37° C. in buffer for a time suitable to remove the peptidoglycan.

Thus, the two-dimensional crystalline array provided as the S-layer from bacterial cells can be recovered, in general, by extraction of nonordered components using detergent; optionally this structure can be cross-linked, and optionally the peptidoglycan may be removed. The preparation can be conducted either on whole cells or on a disruptate, such as a sonicate.

In addition, since the carriers of the invention can be of sufficient size to be retained by a suitable filter, potential pyrogens such as lipopolysaccharides can be removed by filtration of the derivatized carrier.

Carriers comprising immunoactive substances may be combined with other substances and compositions. It is thus possible to achieve various functions of the pharmaceutical composition. For example, strongly hydrophobic carrier molecules can be mixed with aggregates carrying the immunoactive substances causing increased uptake of the pharmaceutical structure by accessory cells.

Carriers comprising different immunoactive substances can be attached to an auxiliary matrix which can be cross-linked to the carriers. Thereby, a pharmaceutical preparation can be generated that would combine different types of carrier molecules such as those differing in their crystalline structures.

Furthermore, carrier aggregates comprising more than one hapten can be used so that the profile of activity of the pharmaceutical composition can be precisely controlled.

In one approach to providing multivalent vaccines of this type, subunits of the carrier aggregate can be separated, conjugated separately to the desired haptens, and then reconstituted to obtain a carrier aggregate with a multiplicity of haptens. For example, in the preferred embodiment using prepared S-layers, separated portions of the S-layer sample can be conjugated to the individual haptens or epitope-containing moiety under the conditions described hereinbelow, and then recombined in the presence of a chaotropic agent such as guanidine hydrochloride or a detergent. Upon removal of the detergent or chaotropic agent by dialysis, the protomers originating from the different portions will self-assemble into an S-layer derivatized with different haptens or immunoactive substances.

ATTACHMENT OF IMMUNOACTIVE MOLECULES

The carriers must be attached to the antigenic determinants to which an immunological response is desired. As used herein, "epitope-bearing moiety" refers to a substance which contains a specific determinant to which the immune response is desired. The epitope-bearing moiety may itself be a hapten—i.e., a simple moiety which, when rendered immunogenic, behaves as an antigen, or may be a more complex moiety, only portions of which are responsible for the immunospecificity with regard to the antibodies obtained. The need for an appropriate carrier is, of course, greater when the epitope-bearing moiety is a hapten, since these simple and low molecular weight substances are only weakly immunogenic. However, the use of the carriers of the invention is applicable to any moiety which contains an epitope to which an immune response is desired.

The two-dimensional crystalline arrays frequently contain glycoprotein and thus the hapten or immunoactive/immunoregulatory substances may be linked to either or both the protein or the carbohydrate portions of the carrier. For two-dimensional crystalline carrier arrays which are composed entirely of protein, linkages to the protein per se must of course be employed.

The choice of the mode of attachment will depend both upon the nature of the haptens and/or immunoactive substances and upon the type of application of the pharmaceutical composition. Under certain circumstances, a mixed mode of attachment can be advantageous.

The immunoactive substances can be attached to the respective carrier molecules directly or by way of bridging molecules such as homo- or heterobifunctional cross-linking agents or peptide chains (e.g., polylysine). The introduction of such spacers or bridging molecules offers the advantage of more precise control of the release of haptens, etc., and of the nature of such fragments as would be formed by enzyme-catalyzed degradation within the endosomes (lysosomes) of macrophages or other accessory cells. Using appropriate spacer groups, preferred sites of cleavage of the immunogenic aggregates may also be introduced. Commercially available homobifunctional or heterobifunctional linkers may be obtained, for example, from Pierce Chemical Co., Rockford, Ill.

By an advantageous process for the production of the pharmaceutical compositions of this invention, such groups on the carrier as would bind the immunoactive substances may be activated prior to attaching the immunoactive substances. Thereby a reliably precise and reproducibly stable attachment of haptens to the respective groups is safeguarded.

For attaching immunoactive substances to carbohydrate portions (glycans) of the S-layer glycoproteins, binding sites within the glycoproteins may be generated by oxidation, e.g., using periodate. Binding sites on the protein portions can also be generated by reacting with glutaraldehyde, the reagent used for cross-linking and activation. Formation of binding sites can also occur by the introduction of active groups, whereby a precise control of the number and kind of binding sites can be achieved. For an especially stable linkage, the haptens can be attached by amide linkages to the carboxyl groups of the protein portion of the carrier. Attachment of the haptens can also be through aldehydes in the form of Schiff bases. The Schiff bases can be reduced to secondary amines.

Binding sites on the immunoactive substances can be activated and the immunoactive substances attached by means of these activated binding sites, to the carriers. This, too, results in stable linkages. This avoids the phenomenon of carriertypic suppression of the immune response.

UTILITY AND ADMINISTRATION

The resulting compositions containing carrier coupled with one or more epitope-bearing moieties are then useful in eliciting an immune response. Administration is by conventional techniques, and the effect of the carrier is to permit the use of weakly immunogenic determinants to generate antibodies or to induce a T-helper response against determinants which, generally speaking, do not elicit such an immune response. Suitable epitope-bearing moieties include those conventionally employed including polypeptides, carbohydrates, nucleic acids and lipids. The proteins, glycoproteins and peptides can include cytokines, hormones, glucagon, insulin-like growth factors, thyroid-stimulating hormone, prolactin, inhibin, cholecystokin or fragments thereof, calcitonin, somastatin, thymic hormones, various releasing factors, as well as antigenic fragments of proteins characteristic of viruses and other infective agents. Various carbohydrates and carbohydrate complexes can be used as well, including bacterial capsules or exopolysaccharides, for example, from Hemophilus influenza B, blood group antigens, and the like. Further, lipid materials can be used such as the steroids or prostaglandins, as well as glycolipids. Other molecules of interest include alkyloids such as vindoline, serpentine, or any other hapten-containing material to which an immune response is sought.

In addition to the ability to raise antibodies, the immune compositions of the invention can be utilized to elicit a T-cell response, as can be verified, as described below, by the ability to elicit a delayed-type hypersensitive (DTH) response in inoculated subjects. Furthermore, T-cells obtained from animals immunized with the compositions of the invention can be transplanted into other animal subjects, resulting in the transfer of immunity to these subjects.

The pharmaceutical compositions of the present invention are particularly suitable as immunizing antigens for achieving high antibody titers and protective isotypes and for immunological memory. When antibodies or fragments thereof are used as epitope-bearing moieties, anti-idiotypic antibodies may be prepared by this method.

The pharmaceutical compositions can be used to advantage for primary immunization and boosting when one and the same immunoactive substance is bound to S-layers derived from two different bacterial strains. Various regimens can be used in administering the compositions of the invention. In typical immunization protocols, a series of injections is employed wherein subsequent injections boost the immune response obtained from the initially injected compositions. The availability of a multiplicity of two-dimensional crystalline carriers permits the use of analogous but different carriers in the series. The problem of inducing carriertypic tolerance is thereby overcome. In some instances, especially where low molecular weight haptens are employed, repeated injections with the hapten conjugated to the same carrier results in a modulated immune response due to this phenomenon. By changing the nature of the carrier, for example, by using S-layers perpared from different microorganisms, this problem can be avoided. Thus, protocols are devised wherein the epitope-bearing moiety is injected first conjugated to S-layer perpared from a first microorganism and followed by injection of the epitope-bearing moiety coupled to a carrier which is composed of an S-layer derived from a second microorganism.

The carrier-epitope moiety complexes are applicable also for use as immunosorbents or as affinity matrices, e.g., for diagnostic kits or extracorporeal depletion of undesirable antibodies from human blood.

The invention will be further explained making reference to the following examples, which are intended to illustrate, not to limit, the invention. In the examples, FIGS. 2–7 are referred to. A more detailed explanation of these figures is given in the section entitled "Figure Legends" which is set forth at the end of the specification herein.

EXAMPLE 1

A. Preparation of the Carrier

Cells of *Clostridium thermohydrosulfuricum* L111-69 (2.5 g) are suspended in 50 mM Tris-HCl buffer, pH 7.1, and sonicated briefly (about 1 minute). Following the addition of a 2% solution of Triton X-100 (12.5 ml), the suspension is incubated at 50° C. for 15 minutes. By this treatment, the cytoplasm and plasma membrane of the organisms is disintegrated whereas the two-dimensional crystalline protein-containing cell wall layer (henceforth termed "S-Layer") and the underlying peptidoglycan layer are conserved as fragments. Subsequently, the mixture is centrifuged at 20,000×g and the pellets washed three times to remove detergent. The pellets are then suspended in 5 mM magnesium chloride solution (25 ml). For removal of cytoplasmic residues and nucleic acids, DNAse (125 ug) and RNAse (500 ug) are added and the whole stirred for 15 minutes at 37° C. The suspension is then centrifuged at 20,000×g and washed three times with water. The pellet is then suspended in 1.1M cacodylate buffer (pH 7.2; 20 ml) and a 50% aqueous solution of glutaraldehyde is added at 40° C. to a final concentration of 0.5%. The suspension is well stirred at 4° C. for a few minutes, centrifuged, and washed with water. The pellet is then suspended in water (25 ml) and Tris-hydroxymethylaminomethane ("Tris") is added to pH=3. Following 10 minutes standing at room temperature, the suspension is again centrifuged (20,000×g) and washed.

Ultrasonic treatment is omitted when the cellular shape of the microorganisms is to be conserved and only the cytoplasmic constituents are to be removed.

When the above procedure is used, the underlying peptidoglycan layer remains associated with the protein-containing cell wall layer. With numerous organisms, this may result in the formation of an additional S-Layer. Thus, the fragments or "ghosts", consisting only of S-Layer and peptidoglycan, now display S-Layers on the inner face of the peptidoglycan layers (FIG. 1); these additional S-Layers can also be coupled to haptens and/or immunoactive substances.

Should the presence of the peptidoglycan be undesirable, the latter can be degraded with a peptidoglycan-degrading enzyme, e.g., lysozyme, and removed. To this end, the material produced as under this section A is treated for 1 h at 36° C. with a solution of lysozyme (0.5 mg lysozyme per ml of a 50 mM solution of Tris-HCl buffer, pH 7.2). In this case, 10 ml of lysozyme solution is added per 0.5 g wet pellet. Depending on the microorganism used, the S-Layer fragments obtained consist of a simple or double S-Layer. Following ultrasonic treatment of cells, open fragments are formed whereas in the absence of ultrasonic treatment, the cellular shape, i.e., the crystalline two-dimensional array is preserved intact.

B. Formation of Binding Sites

The pellet prepared according to A is suspended in water (5 ml) and a 0.1M solution of sodium periodate (5 ml) added. The suspension is allowed to stand for 24 h with exclusion of light to allow oxidation and give rise to the formation of aldehyde functions as binding sites. Subsequently, the suspension is centrifuged and the pellet washed with 10 mM sodium chloride solution, to remove the iodine-containing salts.

C. Binding of Proteins to the Modified S-Layers

The pellet of oxidized material obtained according to B (about 0.2 g) is suspended in water (1 ml) and the suspension is mixed with a solution (1 ml) of bovine serum albumin (50 mg) in water (10 ml). This solution is allowed to stand at room temperature (60 minutes) and is then centrifuged.

Figure 2:
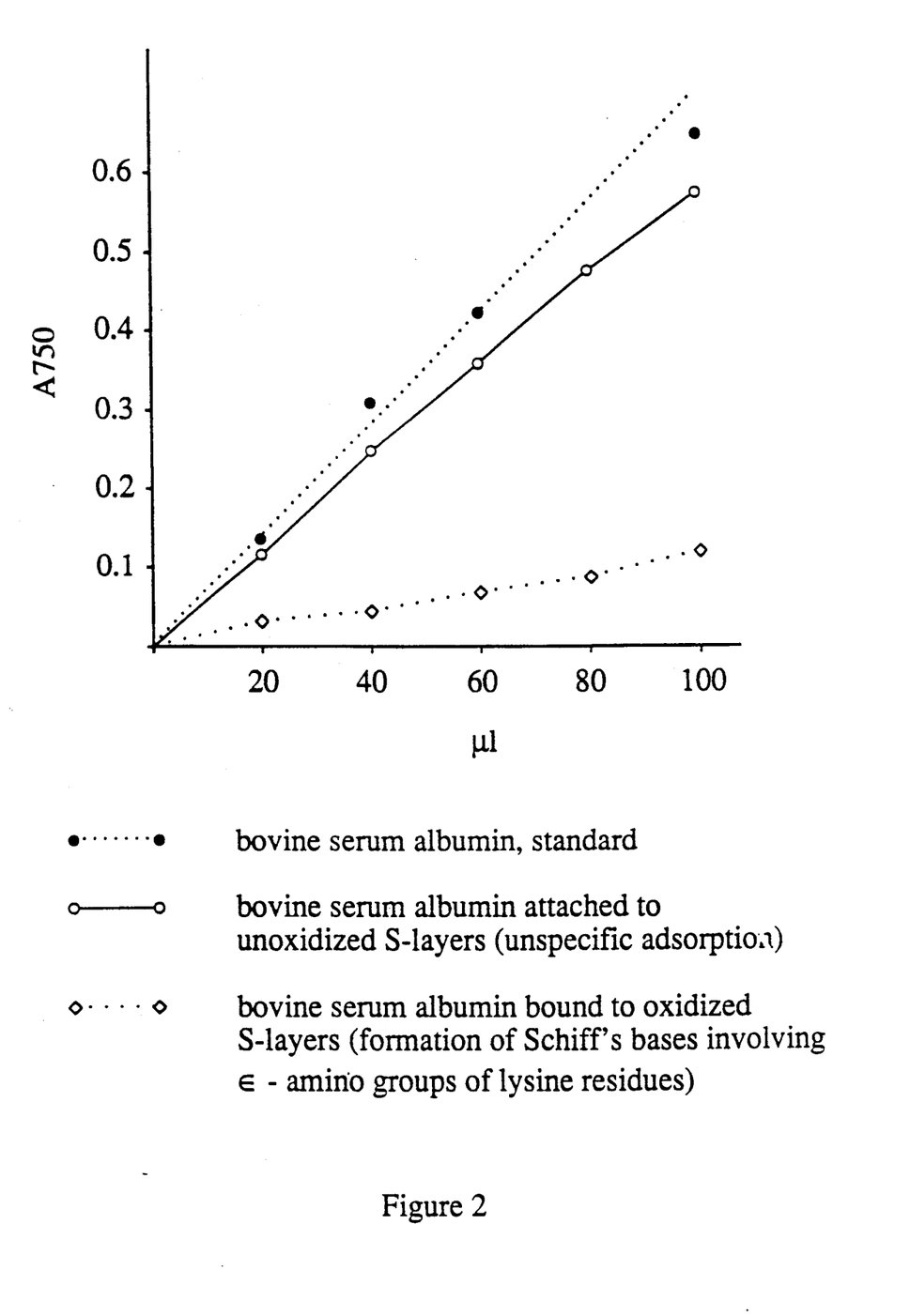
FIG. 2 is a graph illustrating the improved analytical results possible using the coupling methods of this invention.

To determine the amount of albumin bound to the carrier, the extinction at 750 nm is measured relative to that of a preparation wherein the periodate solution has been replaced by water (unoxidized control). The result of this measurement is seen in FIG. 2. Clearly, the attachment to the carrier is significantly higher in the case involving prior oxidation with periodate.

EXAMPLE 2

A. Preparation of the Carrier

Cells of *Bacillus stearothermophilus* PV7.2 (2.5/g) are suspended in 50 nM Tris-HCl buffer, pH 7.2, and sonicated for about 1 minute. Following addition of 2% Triton X-100 (12.5 ml), the suspension is incubated for 15 min. at 50° C. By means of this treatment, the cytoplasm of the cells is disintegrated while the S-Layer and the peptidoglycan layer are preserved. Thus, fragments are formed which correspond in shape more or less to the original shape of the bacterial cell (so called "ghosts").

Subsequently, the suspension is centrifuged at 20,000×g and the pellet washed three times with water to remove the detergent. The pellet is then suspended in 5 mM magnesium chloride solution (25 ml), DNAse (deoxyribonuclease, 125 μg) and RNAse (ribonuclease, 500 μG) are added, and the mixture is stirred at 37° C. for 15 min. Subsequently, the pellet is washed three times with water, centrifugation in between being at 20,000×g. The pellet is then suspended in 0.1M cacodylate buffer (pH 7.2) and the suspension mixed with a 50% solution of glutaraldehyde in water at 4° C. to a final concentration of 0.5%. The suspension is then vigorously stirred at 40° C. for a few minutes, centrifuged, and the pellet washed with water. Where glutaraldehyde residues are linked through only one of their two aldehyde functions, the remaining aldehyde function can serve as a binding site. This provides aldehyde functions for binding, similar to those of the oxidation products described under Example 1B.

B. Binding of Protein(s) to the Modified S-Layers

The modified S-Layers prepared in section 2A are mixed with a solution of bovine serum albumin as in Example 1C, and the amount of protein bound is determined as described there.

EXAMPLE 3

A. Preparation of the Carrier

Cell walls of *Clostridium thermohydrosulfuricum* L111-69 are treated with glutaraldehyde (0.5% in 0.1M sodium cacodylate buffer, pH 7.2) for 20 minutes at 20° C., so as to stabilize the outermost cell wall layer (S-layer). The reaction is terminated by the addition of excess ethanolamine. During cross-linking the cell wall fragments may be either in suspension or attached to a porous surface (e.g., an S-Layer ultrafiltration membrane). The cell wall fragments are then washed with distilled water to remove the reagent mixture.

B. Creating Binding Sites for Ligands Containing Thiol (SH) Groups

The pellet of a cross-linked preparation as under A above, is suspended in distilled water (30 ml) and to the suspension is added 1-ethyl-3,3-(dimethylaminopropyl)-carbodiimide (EDAC; 60 mg) maintaining a pH of 4.75. This step activates the exposed carboxyl groups of the S-Layer. Subsequently, an excess of hexamethylenediamine (0.5 g) is added and the pH kept at 8.0 for 60 minutes. Subsequently, the reaction is terminated by addition of acetic acid. The suspension is centrifuged at 20,000×g and the pellet washed three times with distilled water. The wet pellet (100 mg) is suspended in 50 mM phosphate buffer, pH 7 (9 ml) and a solution of meta-maleimidobenzoyl-N-hydroxysuccinimide ester (50 mg per ml of tetrahydrofuran; 1 ml) is added. The mixture is then incubated for 30 minutes at 20° C.

C. Binding of SH-Containing Proteins to the S-Layers Derivatized as Under B

Following centrifugation at 20,000×g, the pellet is suspended in 50 mM phosphate buffer (pH 7.0), β-galactosidase (20 mg) is added and the mixture is incubated for 2 h at 20° C. After centrifugation at 20,000×g and repeated washing with phosphate buffer, the activity of the β-galactosidase covalently linked to the protein matrix is determined.

The reactions of the Example are summarized as follows:

1.

2.

3.

4.

treated with glutaraldehyde, as described in Section A of Example 3, to stabilize the outermost cell surface.

B. Generating the Binding Sites

The cell wall fragments from Section A (100 mg) are suspended in anhydrous tetrahydrofuran (THF), incubated at 20° C. for 10 minutes, centrifuged at 20,000×g and suspended again in a 2.5% solution of cyanogen bromide in anhydrous tetrahydrofuran (10 ml). Following incubation for 2 h, the cell wall fragments are separated by centrifugation at 20,000×g and washed with THF for removal of residual reagent.

C. Binding of Proteins to the Derivatized S-Layer

The pellet is suspended in 50 mM phosphate buffer (pH 8.0 (10 ml), containing invertase (20 mg) and incubated for 18 h at 4° C. Following centrifugation at 20,000×g, the pellet is washed twice with phosphate buffer and the enzyme activity of the invertase bound to the protein matrix determined.

The reactions of this Example are summarized as follows:

$$\text{—OH} \atop \text{—OH} \quad + \text{ BrCN} \longrightarrow \quad \begin{array}{c} \text{—O} \\ \text{—O} \end{array} \!\!\! \diagdown \!\! C = NH \; +$$

(cyclic imidocarbonate)

EXAMPLE 4

A. Preparation of Carrier

For the coupling of invertase, the vicinal diol groupings of the carbohydrate portion (glycan) of S-Layer glycoprotein are utilized. Cell wall fragments are -continued (N-substituted carbamate)

EXAMPLE 5

A.

Cell wall fragments of *Clostridium thermohydrosulfuricum* L111-69 are cross-linked with glutaraldehyde as described in Example 3, section A.

B. Generating the Binding Sites

Cell wall fragments (0.1 g) are suspended in anhydrous dimethylformamide (DMF, 20 ml) and EDC (60 mg) and N-hydroxysuccinimide (0.5 g) are added to the suspension. Following incubation for 1 h, the suspension is centrifuged at 20,000×g and washed twice with DMF.

C. Binding of Proteins to the S-Layer Thus Modified

The pellet obtained as under 5B is suspended in 0.1M sodium hydrogencarbonate (pH 8.8) containing dissolved dextranase (20 mg) and the reaction mixture is incubated at 4° C. for 18 h. The cell wall fragments containing the bound dextranase are obtained by centrifugation at 20,000×g and washed twice with distilled water. The dextranase activity contained in the pellet is then determined.

The reactions of this Example are summarized as follows:

EXAMPLE 6

Coupling of a Synthetic Carbohydrate Antigen to Oxidized S-Layers

A. Preparation of Carrier and Generation of the Binding Sites

The preparation of the oxidized glycoprotein S-Layers was performed as described in Example 1, section A and B.

B. Binding of the Carbohydrate Antigen to the Carrier

The oxidized (polyaldehyde) derivative of the S-Layer prepared in Section A is incubated with the 3-(2-aminoethyl)thiopropyl glycoside of a disaccharide whereby Schiff base formation occurs. This step can also be performed with any other saccharide attached to an aglycone that contains amino groups.

These reactions are shown as follows:

[3-(2-amonioethyl)thiopropylglycoside of a disaccharide consisting of two 3-deoxy-D-mano-2-octulopyranosylono residues]

General recipe for the preparation of 3-(2-aminoethylthio)propyl glycosides from allyl glycosides.

A solution of the allyl glycoside (5 mM) in a solution of cysteamine hydrochloride (15 milliequivalents of SH-groups in 10 ml) is allowed to stand for 1.5 h at room temperature. The duration of this reaction may vary. The reaction mixture is subsequently separated over a column of cation exchange resin (e.g., Rexyn 101, ammonium form, 200-400 mesh). The column is eluted with water, 0.5M ammonia, and 1.0M ammonia. Unreacted allyl glycoside appears in the aqueous eluate, and the 3-(2-aminoethylthio) propyl glycoside is eluted in the fraction corresponding to 1.0M ammonia. Those fractions containing products are subsequently evaporated to dryness.

The Schiff base derivative of the S-Layer, as obtained by binding of the 3-(2-aminoethylthio)propyl glycoside can be used directly for binding of antibodies. These can be assayed directly if they are labelled with ferritin, horseradish peroxidase, $^{125}I$ (iodine-125) or in any other appropriate manner. The bound antibodies can also be assayed via a so-called "sandwich" method by binding of labelled antibodies directed against the first, hapten-bound antibodies.

The Schiff base derivative of the S-Layers as obtained by binding of the 3-(2-aminoethylthio)propyl glycoside may be converted into a secondary amine derivative of the S-Layers by reacting it with borohydride or another suitable reducing agent.

C. Determination of Free Aldehyde Groups

The determination of the content of free aldehyde groups in the polysaccharide portion, following oxidation with periodate, is performed using phenylhydrazine or 2,4-dinitrophenylhydrazine, or other suitable reagents.

After oxidation with sodium metaperiodate as above described, iodine-containing salts are removed by dialysis against water. Subsequently, a solution of the corresponding hydrazine reagent in 10% acetic acid is added and the mixture is allowed to react for 1 h. Then the excess reagent is removed by dialysis and the amount of hydrazone groups determined by colorimetry. This method can also be applied to determine residual free aldehyde groups after binding of a hapten containing amino groups, or of the immunoactive substances.

EXAMPLE 7

A. Preparation and Structure of S-Layer Glycoprotein

A cross-linked S-Layer preparation from cell wall

The secondary amine derivative of the S-Layer would be more stable to acid than the Schiff base derivative.

The determination of the content of free aldehyde groups in the polysaccharide portion, following oxidation with periodate, is perforemd using phenylhydrazine or 2,4-dinitrophenylhydrazine, or other suitable reagents.

Suitable carbohydrate-containing S-Layers are oxidized with sodium metaperiodate as described in Example 1, sections A and B. Iodine-containing salts are removed by dialysis against water. Subsequently, a solution of the corresponding hydrazine reagent in 10% acetic acid is added and the mixture is allowed to react for 1 h. Then the excess reagent is removed by dialysis and the amount of hydrazone groups determined by colorimetry. This method can also be applied to determine residual free aldehyde groups after binding of a hapten-containing amino groups, or of the immunoactive substances.

fragments of *Clostridium thermohydrosulfuricum* L111-69 (hereinafter L111) and *Bacillus stearothermophilus* NRS2004/3A (hereinafter 3A) were prepared using the procedure set forth in Example 1A. Electron microscopic studies of these compositions show that both the "L111" and "3A" preparations exhibit an S-Layer lattice on either face of a peptidoglycan sacculus (FIG. 1).

The peptidoglycan of the foregoing preparations was removed by digestion with lysozyme as described in Example 1A to provide a double layer of S-Layer glycoprotein fragments held together by the penta-1,5-diylidene bridges resulting from the glutaraldehyde cross-linking. Each morphological unit of the S-Layer lattice consists of six identical subunits in the 3A preparation. An additional S-Layer preparation from *Bacillus alvei* CCM2051 (hereinafter 2051), prepared from whole cell walls as described in Example 3, part A, cross-linked with glutaraldehyde and digested with lysozyme as described in Example 1A also showed two identical subunits.

B. Specific Methods for Attachment of Haptens

1. Periodate Oxidation

The glycan chains of the L111 preparation are known to consist of approximately 60 disaccharide repeats of 4(-α-D-Manβ-(1-3)-α-L-Rhap-(1, which comprises about 10% of the S-Layer glycoprotein. When treated with periodate at 0.1M for 2-5 h at pH 5.5, the mannose residues were oxidized completely as estimated by the phenol-sulfuric acid assay. Decreasing the pH value to 4.5 shortens the oxidation times and up to 23 molecules of a carbohydrate hapten linked to a spacer terminating in a primary amino function (for example, A-trisaccharide) per S-Layer protomer was achieved. However, the resulting Schiff bases must be stabilized by reduction with, for example, sodium borohydride.

The 3A S-Layer protomers have two different glycan chains and the total carbohydrate content is about 7.5%. These glycans have the structures:

-2)(-α-L-Rhap-(1-2)-α-L-Rhap-(1-3)-β-L-Rhap(1, having about 50 repeats; and
-4)(-β-ManpUA2,3(NAc)2-(1-3)-α-GlcNAc-(1-4)-β-ManpUA2,3(NAc)2-(1-6)-α-Glcp-(1, having approximately 15 units.

Oxidation of this S-Layer preparation under the same conditions as above provided binding sites for up to 17 molecules of hapten per S-Layer subunit. Unfixed S-Layers gave lower yields of conjugates or hapten contents.

2. Epichlorohydrin Activation

Glutaraldehyde-fixed S-Layer fragments (2–3 mg) were suspended in 2.5 mL of either 0.2M sodium bicarbonate/sodium carbonate buffer, pH 9.1–10.0, or 0.2M sodium carbonate solution pH 11.4; or 0.4 sodium hydroxide solution) containing 25 mg sodium borohydride. Upon addition of epichlorohydrin (0.2 mL), the reaction mixtures were incubated for 30 min to 16 h at room temperature or 40°, with rotation on a rotary evaporation (150 rpm). Blanks were prepared similarly, but either epichlorohydrin or hapten was omitted.

After centrifugation and washing with water (5×1.5 mL) to remove all of the activating agent, the combined supernatants of the first centrifugation and all washes were analyzed for carbohydrate material shed into the supernatant from the S-Layers under the strongly alkaline reaction conditions. The remaining pellets were suspended in hapten solution (1.0–1.4 mL, 1–2 μmoles/mL 0.2M sodium bicarbonate solution) and incubated for 2–6 h with shaking on a hematology mixer at room temperature. Excess of hapten was removed by washing with water (5×1.5 mL) prior to the blocking of unreacted epoxy groups by treatment with 0.02M ethanolamine in 50 mM sodium bicarbonate solution for 4–18 h at room temperature. Subsequently, the samples were washed with water (5×1.5 mL), lyophilized and assayed for carbohydrates, as described for the S-Layer conjugate prepared via periodate oxidation.

3. Divinylsulfone Activation

Glutaraldehyde-fixed S-Layer fragments (2–3 mg) were suspended in 2 mL of appropriate buffer (see epoxy activation, pH 9.1–11.4) and then divinyl sulfone (0.2 mL) was added to the suspensions. Treatment of blanks, estimation of shedded S-Layer glycan, incubation times with hapten solutions, and blocking of unreacted vinyl groups was performed exactly as described for the epoxy activation.

4. Activation with 1-Ethyl-3-(3-Dimethylaminopropyl)-Carbodimide (EDAC)

Two different reaction conditions were used:

i) About 3 mg of glutaraldehyde fixed S-Layer fragments were suspended in 3 ml of water. Then the pH was adjusted to ca. 4.6 using diluted HCl. After addition of 10 mg EDAC the pH was readjusted with HCl to 4.67–4.70. The suspensions were stirred at room temperature for 1 h while the pH should not change. Excess of EDAC was then removed by washing with ice-cold water (2×10 ml) and centrifugation (19,000 rpm, 4° C.). The pellets were incubated with hapten solution (1.0–1.5 mL, ca. 2 μmoles mL$^{-1}$/0.2M NaHCO$_c$) at room temperature for 2–18 h. Upon washing with water (5×1.5 mL) the samples were lyophilized and assayed.

ii) About 3 mg S-Layer material was suspended in 2 mL of 0.1M phosphate buffer (pH 4.0–4.7) and 10 mg EDAC was immediately added to the suspensions. After activation for 1 h with rotation on the rotavapor 1 mL hapten solution was added and the mixture was incubated overnight in the presence of EDAC at room temperature. After washing with water (5×1.5 mL) activated free carboxyl groups were blocked with 10% glycine in 0.2M NaHCO$_3$ for 1–2 h at room temperature. The samples were then washed, lyophilized and assayed.

Up to 60 moles of hapten, immobilized to the carboxyl groups of the protein was found on strain L111-69 and the difference observed between both methods was minimal. With strain NRS 2004/3a the overnight incubation in the presence of EDAC increased the amount of immobilized haptens from 14 to 32 moles per mol.

EXAMPLE 8

Preparation of T-Disaccharide Antigen Conjugates

T-disaccharide is a tumor marker of the formula βGalp(1-3)αGalNAcp. A composition containing this disaccharide as a hapten was prepared by coupling the spacer-linked disaccharide of the formula βGal-(1-3)αGalNAc-O(CH$_2$)$_8$CNANA$_2$ to S-Layers by either of the general procedures described under Example 7.B.4.

EXAMPLE 9

Immobilization of Synthetic Carbohydrate Antigens Onto Unfixed Oxidized S-Layers A. A Formation of Binding Sites Two identical suspensions are prepared of purified, unfixed cell walls of *Clostridium thermohydrosulfuricum* L111-69 in water (0.25 mL; 0.25 g/ml).

Each suspension is mixed with cold (4°) 50 mM sodium acetate buffer, pH=5.0 (0.25 ml). To one of the suspensions is added a cold 0.2M solution of sodium periodate in 50 mM sodium acetate buffer, pH=5.0 (0.5 mL), and the resulting suspension is stirred for 3 h at 4° with exclusion of light (500 rpm). The other suspension is not oxidized, but mixed with 50 mM sodium acetate buffer (0.5 mL) and subjected to analogous workup. Following the oxidation period, the suspensions are centrifuged (30,000×g, 10 min) and washed once with sodium acetate buffer, pH=5, and twice with 0.2M sodium borate buffer, pH=8.5, to remove iodine-containing materials.

B. Binding of Carbohydrate Antigen to Carrier

The polyaldehyde product of oxidation of the S-Layers (carrier formed as under A) is suspended in sodium borate buffer, pH=8.5 (2 mL) together with sodium cyanoborohydride (10 mg). T-disaccharide (hydrazide form, 5 mg) is added to one of the oxidized samples, while one oxidised and one unoxidized sample are processed without hapten addition. The preparations are incubated at 37° for 24 h with stirring (500 rpm). Subsequently, the S-Layers are washed once with 0.2M borate buffer, once with 0.2M sodium chloride solution, and twice with distilled water. The centrifugation pellets of the respective samples may then be frozen for storage, or processed further. During this procedure, the immobilization of the haptens occurs by way of reductive amination on oxidized, unfixed S-Layers. The presence of the peptidoglycan layer provides for a stabilizing influence similar to the one exerted by glutaraldehyde fixation of the S-Layer protein.

C. Degradation of Peptidoglycan in a (Sterile) Ultrafiltration Cell

The (frozen) S-Layer pellets (produced according to B) are suspended in 50 mM Tris-hydrochloride buffer pH=7.2 (5 mL) in a 10 mL ultrafiltration cell (AMICON) equipped with a magnetic stirrer and an ultrafiltration membrane (e.g. BIOFIL ™ produced from S-Layers of Bacillus stearothermophilus PV72). The suspension is mixed with lysozyme (5 mg) and incubated at room temperature for 90 min with stirring (500 rpm). Subsequently, pressure is applied to the cell (0.2 MPa) whereby the high molecular weight S-Layer protein (containing the bound hapten) becomes enriched in the supernatant. The turbid suspension is washed with water (ca. 60 mL) to remove degraded peptidoglycan and lysozyme (until no extinction is detectable at 280 nm). To test for possible loss of (haptenated) S-Layer material, all washes were combined, dialyzed exhaustively against water, lyophilized, and analyzed by SDS-polyacrylamide gel electrophoresis (SDS-PAGE). This analysis has confirmed the absence of S-Layer materials from the wash fluids.

D. Purification of S-Layer-Hapten Conjugates

The enriched suspension in the ultrafiltration cell (ca. 1 mL) is mixed with 5M guanidine hydrochloride (5 mL) and incubated for 1 h at room temperature with stirring. By this treatment, the S-Layers are dissociated into protomers (MWA ca. 100 kDa) and protein impurities are dissolved. The process is accompanied by a clearing of the suspension. The protein-containing solution is enriched by the application of pressure (0.2 MPa) with stirring (500 rpm) and the guanidine hydrochloride washed out with water until extinction at 280 nm is no longer detectable. The clear washes were combined, dialyzed and analyzed for S-Layer fragments by SDS-PAGE. During washing of the clear solution in the filtration cell, the S-Layer protein reaggregates. The suspension is removed from the cell, lyophilized and examined by SDS-PAGE. The aggregates consist only of S-Layer protein containing bound hapten. The quantity of bound hapten is estimated by the difference in phenolsulfuric acid reactivity between the activated and non-activated samples.

Using this process for immobilization of hapten on an unfixed S-Layer, followed by the removal of the peptidoglycan and filtration over an ultrafiltration membrane of defined pore size, S-Layer-hapten-conjugates are produced aseptically in a sterilizable reaction vessel. By virtue of special precautions, the starting material (S-Layer-containing cell walls) is practically free of lipopolysaccharide (LPS; endotoxin) contaminations; moreover, LPS fragments would conceivably be removed during filtration after dissociation of the S-Layer protein. Therefore, the S-Layer hapten conjugates thus obtained can be considered pyrogen-free.

EXAMPLE 10

Efficacy of the T-Disaccharide S-Layer Compositions

Figure 3:
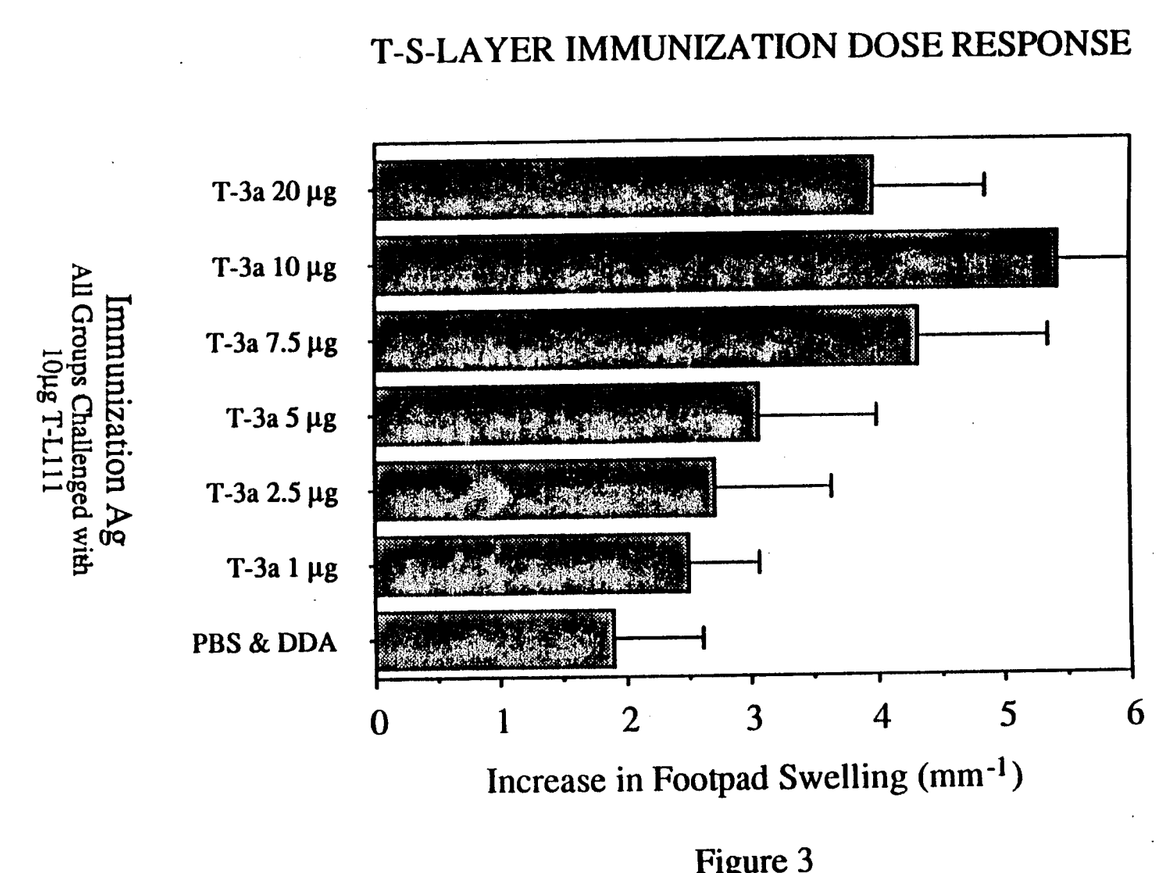
FIG. 3 is a graph illustrating the dose response of the T-disaccharide linked S-layer needed to prime a delayed-type-hypersensitivity (DTH) response.

Groups of 5–10 mice were pretreated with cyclophosphamide (CP) and two days later were immunized with the T-disaccharide coupled, 3a-S-Layer preparations described in Example 8. Injection was made intramuscularly into the hind leg muscle. Seven days later, the mice were footpad-challenged with the T-disaccharide-coupled L111 S-Layer preparation, also prepared according to the procedure outlined in Example 8. Changes in footpad thickness were determined 24 h later using a Mitutoyo Engineering micrometer. By varying the amounts of T-disaccharide-3a-S-Layer administered, it was found that the minimum concentration of T-disaccharide-3a S-Layer required to prime the mouse for a subsequent DTH response to challenge with T-disaccharide-L111 was 5 µg/mouse, and a maximal response was obtained when immunization was performed at 10 µg of disaccharide T-disaccharide-3a-S-Layer per mouse (FIG. 3). At this level, a footpad swelling of approximately 5.5 mm$^{-1}$ was obtained. An increase in the dose to 20 µg resulted in a lowering of swelling to 4 mm$^{-1}$.

Figure 4:
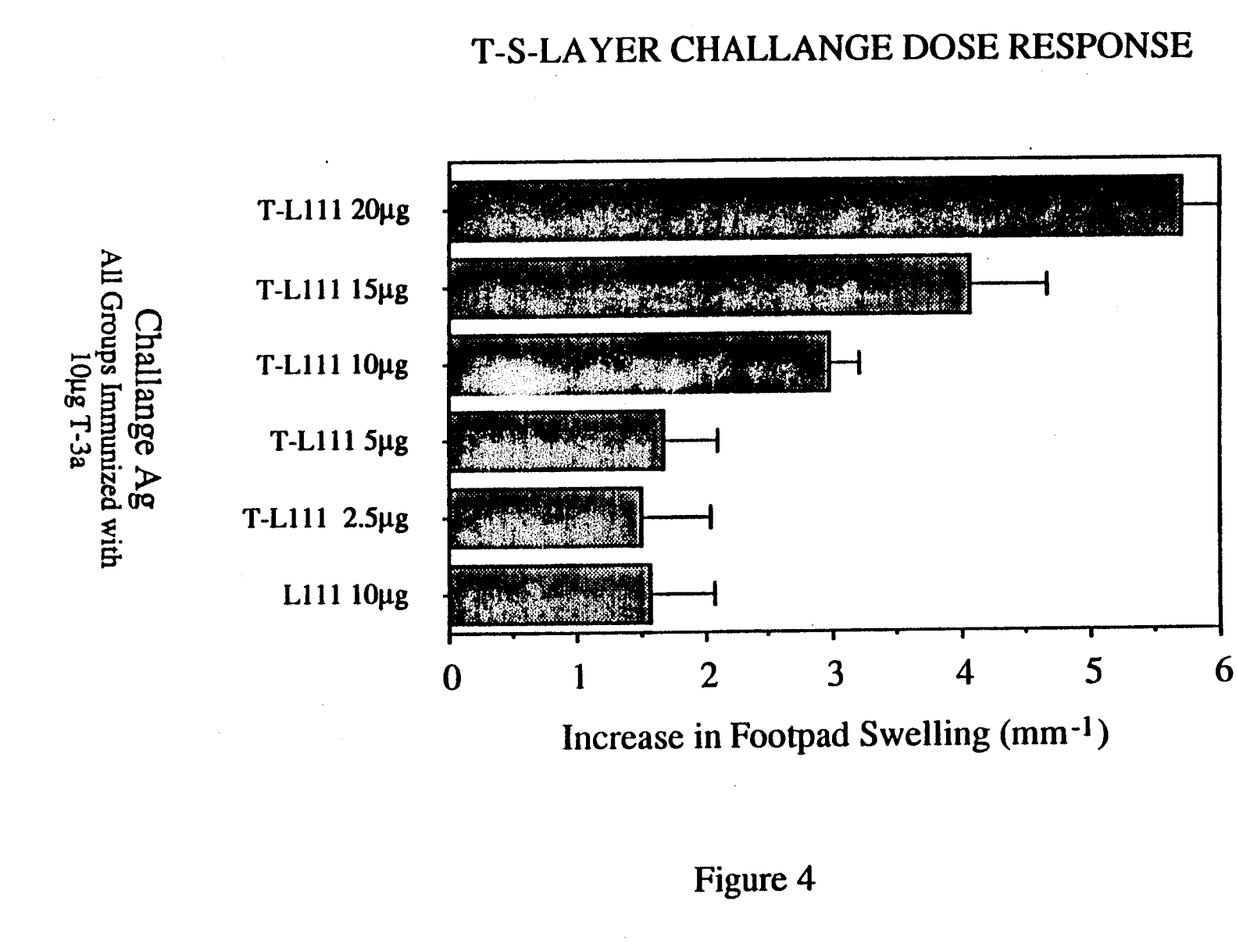
FIG. 4 is a graph illustrating the amount of T-disaccharide needed to elicit a DTH response in primed mice.

In further experiments, CP-pretreated mice were immunized with 10 µg of T-disaccharide-3a-S-Layer, and seven days later were footpad-challenged with varying amounts of T-disaccharide L111 S-Layer. Maximum response (4.5 mm$^{-1}$) was obtained using 20 µg of T-disaccharide L111 S-Layer (FIG. 4).

The foregoing results show that the T-disaccharide S-Layer preparations induced a hapten-specific cellular response to the carbohydrate hapten, and give results comparable to the response seen with strong immunogens such as complex viral antigens.

EXAMPLE 11

Specificity of the T-Cell Responses Generated by S-Layer Conjugates

A further control confirmed that the DTH reponse was specific to the T-disaccharide hapten. In these controls, CY-pretreated mice were immunized with T-disaccharide-3a-S-Layer in the presence of 100 µg dimethyldioctadecyl ammonium bromide (DDA). They were then challenged with PBS and with L111 S-Layer lacking the T-disaccharide, as well as T-disaccharide L111 S-Layer. The results are shown in Table 1. Only the T-disaccharide-L111 resulted in significant swelling. Thus, the results show an absence of cross-reactions between different S-Layer preparations and make it possible to utilize different S-Layers for multiple immunization with the same hapten.

This can be useful in immunotherapy or in immunopotentiation of the immune response to weak antigens, avoiding the phenomenon of carrier-typic suppression.

TABLE 1

| Specificity of the Haptenated S-Layer | | |
|---|---|---|
| Immunization Antigen[a] | Challenge Antigen | Footpad Swelling (mm × 10$^{-1}$) |
| T-3a 10 µg/mouse | PBS | 0.8 ± 0.8 |
| T-3a 10 µg/mouse | EDAC L111 10 µg/mouse[b] | 0.37 ± 9.4 |
| T-3a 10 µg/mouse | T-L111 10 µg/mouse | 3.8 ± 0.8[c] |
| PBS & DDA | T-L111 10 µg/mouse | 1.89 ± 0.65 |
| NT | T-L111 10 µg/mouse | 1.33 ± 0.4 |

[a]CP-pretreated mice were immunized with antigen mixed with 100 µg DDA.
[b]L111 was sham-treated with EDAC to control for the possible modification of L111 by the EDAC reagent.
[c]Significantly different from all other groups P > 0.001.

EXAMPLE 12

Comparison to Other Carriers and Adjuvant Systems

Figure 5:
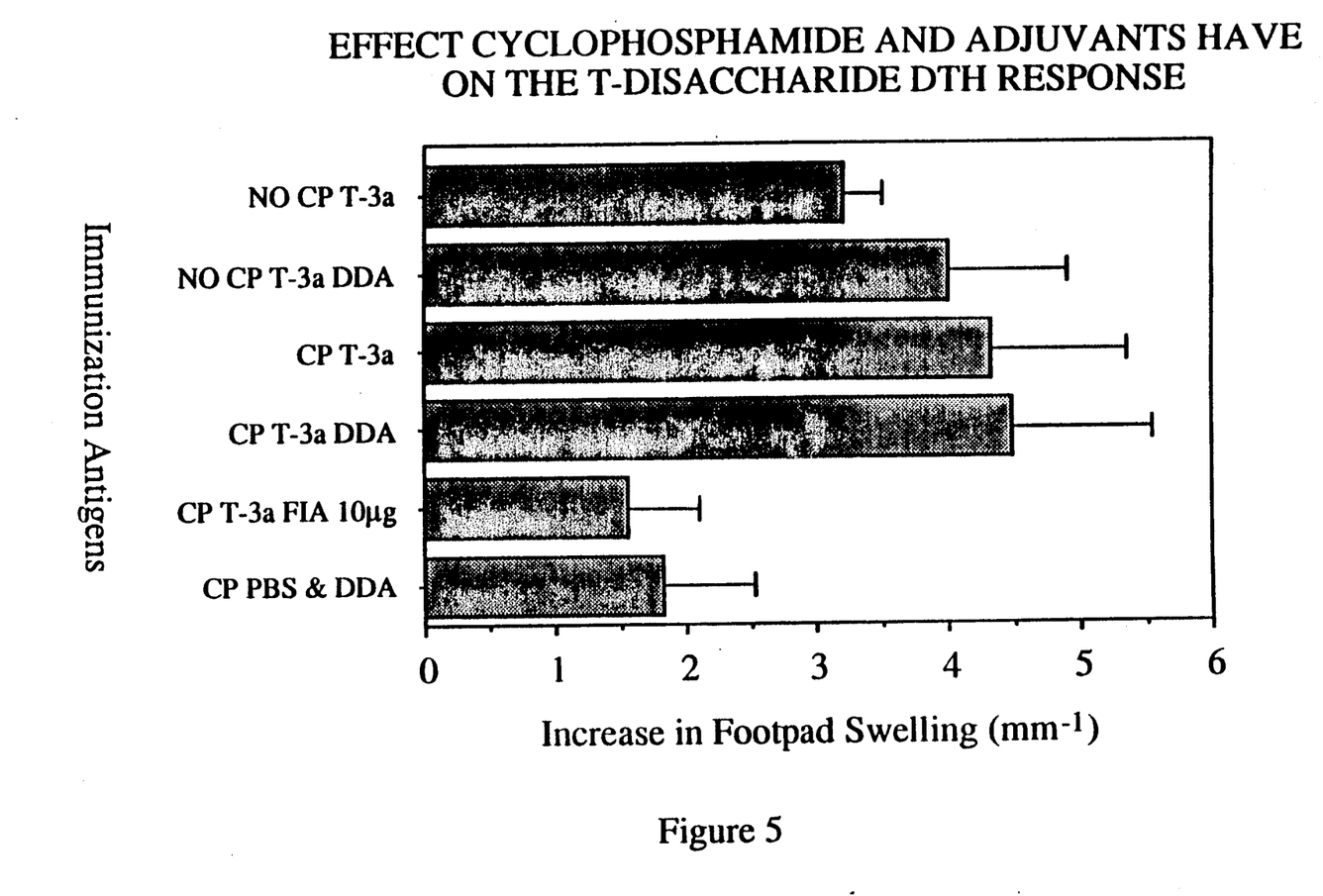
FIG. 5 is a graph illustrating the effect adjuvants have on the T-disaccharide S-layer response.

The immunization protocols of Example 10 were followed where mice were CP treated or not, then immunized with T-disaccharide-3a-S-Layer. DDA or Freund's Incomplete Adjuvant (FIA) were used as adjuvants. Seven days after immunization, the mice were footpad-challenged with T-disaccharide-L111 (analogous S-Layer preparations according to Example 10), and the footpad swelling was measured 24 h later. These results indicate that although T-disaccharide-3a is effective in priming for DTH, the strongest response is observed when mice were treated with CP (FIG. 5). The results also show that T-disaccharide-3a is best administered in conjunction with DDA, in contrast to no adjuvants or FIA. To compare the immunopotentiating response of S-Layers with other carriers, mice were immunized as outlined in example 10 using T-disaccharide-3a-S-Layers, T-disaccharide bovine serum albumin (T-disaccharide BSA) or 8-methyloxy carbonyal octanol (the linker arm attached to the T-disaccharide) linked to BSA. Seven days after immunization, mice were footpad challenged with T-disaccharide-L111 according to example 10. The results in FIG. 6 demonstrates the immunopotentiating properties of the S-Layer carrier, since administration of the T-disaccharide coupled to Bovine serum albumin (BSA) produced no DTH response. Although other workers have reported DTH responses to carbohydrate antigens, the protocols were complex, and a DTH response could not be obtained by immunization with hapten conjugates alone. The foregoing results provide evidence for DTH against the T-disaccharide by a single immunization with the T-disaccharide conjugated to S-Layer.

EXAMPLE 13

Induction of In-Vitro Lymphoproliferative Response

The mice immunized with both T-disaccharide-3a and T-disaccharide-L111, as described above (using DDA after CP treatment), were sacrificed, and the immune lymphocytes were isolated and cultured. The isolated lymphocytes were then cultured with varying amounts of 2051 S-Layer, T-disaccharide-2051, T-disaccharide-BSA, or T-disaccharide-KLH. As shown in Table 2, only T-2051 was capable of inducing a response, as measured by tritiated thymidine uptake. The response was dose dependent and peaked at 10 μg/ml. The failure of T-disaccharide-KLH or T-disaccharide-BSA to elicit a blastogenic response may be explained by the notion that the S-Layer conjugate may be taken up preferentially by the macrophages because S-Layers take on the shape of bacteria.

TABLE 2

Stimulation of Lymphocytes from Mice Immunized with Both T-Disaccharide-3a and T-Disaccharide-L111

| Antigen in Culture 20 μg/ml | CPM $^3$II-Thymidine Uptake | Statistical Probabilities[a] |
|---|---|---|
| PBS | 2303 ± 692 | tND |
| 2051[b] | 2549 ± 1258 | NS[c] |
| T-BSA | 1840 ± 866 | NS |
| T-KHL | 2091 ± 498 | NS |
| T-2051 | 4654 ± 1294 | P = 0.001[b] |

[a]All statistics were compared to the PBS values.
[b]2051 is the unbound S-Layer isolated from *B. alvei* and is the control for the T-disaccharide-bound 2051.
[c]NS not significant
[d]P < 0.01 when compared to 2051 stimulation alone.

EXAMPLE 14

Transfer of Activated Lymphocytes

Figure 7:
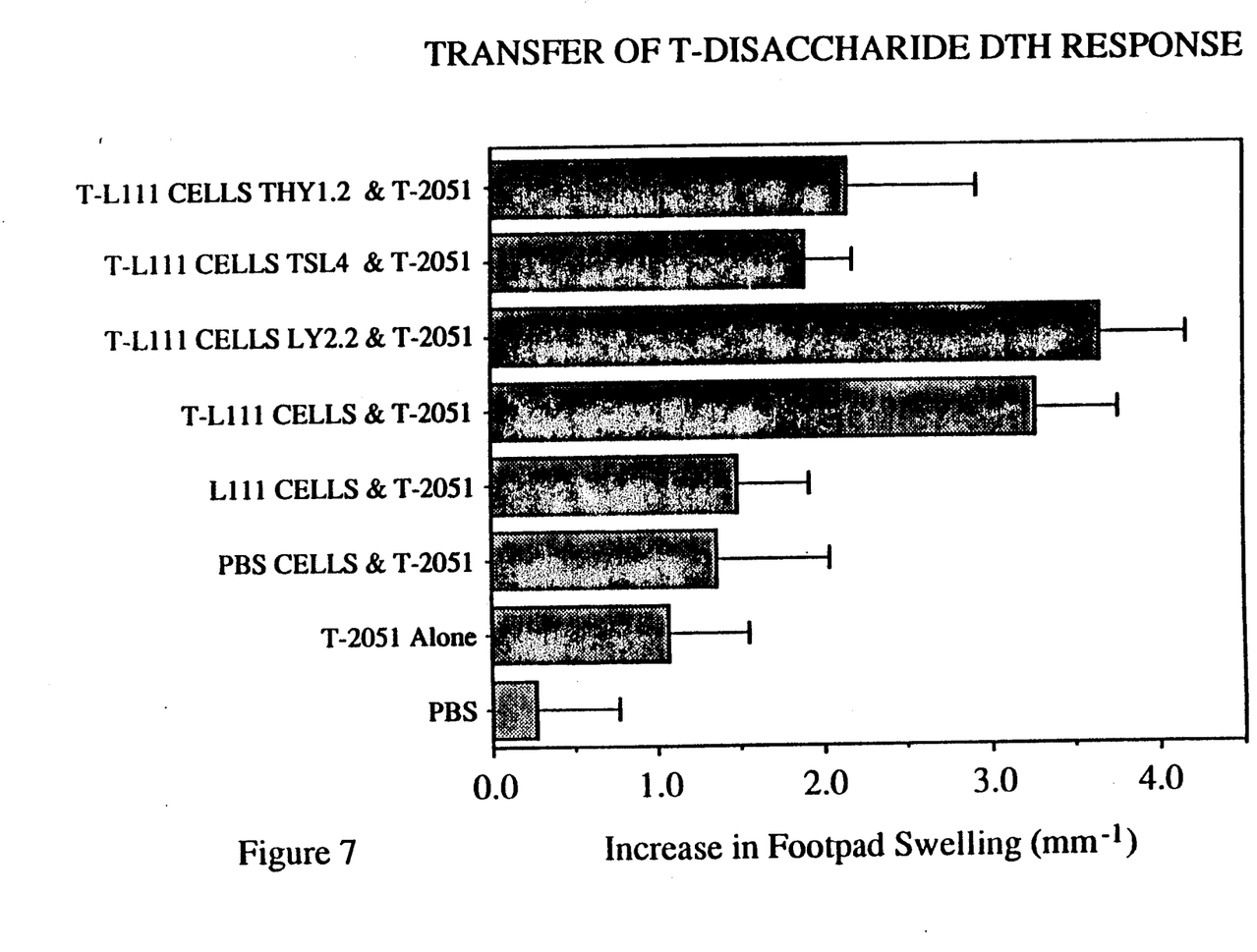
FIG. 7 shows data indicating that T-cells stimulated by immunization with the invention compositions can transfer the capacity to exhibit DTH.

To clearly show that the DTH reponse generated by the T-disaccharide conjugate was actually due to helper T-cells, an adopted transfer experiment was carried out. In these series of experiments CP-pretreated mice were immunized with 10 μg of T-3a in DDA, sacrificed seven days later, and their draining lymph nodes and spleens removed. Primed lymphocytes were then isolated and cultured for three days with T-L111 and control antigens. The stimulated cells were then depleted of the specific populations of T-cells by treatment with monoclonal antibodies and complement. The depleted, bulk-stimulated cells were then washed, mixed with T-S-Layer 2051 or PBS, and injected into the hind footpad of naive mice. The DTH reponse was then measured 24 h later. The results of this experiment are shown in FIG. 7. It can be seen that a strong DTH response was observed in the mice adoptively transferred with primed cells stimulated with T-disaccharide-L111 and mixed with T-disaccharide-2051. However, the similarly primed cells stimulated with L111 alone and then mixed with T-disaccharide-2051 did not induce a strong DTH response. Even though the primed lymphocytes at one point were exposed to all three different S-Layers, no cross-reactive DTH reponse directed towards the S-Layer was observed. Only when the three S-Layers were haptenated with the T-disaccharide was a significant DTH response observed. Also, when the primed lymphocytes were depleted of specific T-cell populations, it became evident that the primed cells involved in the DTH repsonse were helper T-cells.

The pharmaceutical structures constituting the embodiment of the present invention are particularly suitable as immunizing antigens for achieving high antibody titres and protective isotypes. When antibodies are used as immunoactive substances, anti-idiotypic antibodies may be prepared by this method. Furthermore, the pharmaceutical structures can be used to advantage for primary immunization and boosting when one and the same immunoactive substance is bound to S-Layer proteins or glycoproteins derived from two different strains. The structures are applicable also as immune sorbents or affinity matrices, e.g., for diagnostic kits or extracorporeal depletion of undesirable antibodies from human blood.

While the invention has been described with reference to the above embodiments, it will be understood that its scope is defined by the following claims.

FIGURE LEGENDS

FIG. 1. Preparation scheme of glutaraldehyde-fixed S-Layer fragments; (a) intact bacterial cell; (b) empty peptidoglycan sacculus after glutaraldehyde fixation. A second S-Layer has been formed on the inner surface; (c) glutaraldehyde-fixed S-Layer fragments after lysozyme treatment consisting of two S-layers. PG, Peptidoglycan; CM, cytoplasmic membrane; S, S-layer - iS and oS, inner and outer S-Layer.

FIG. 3. Effect of the dose of T-disaccharide-linked to *B. stearothermophilus* S-Layer (T-3a) on the immunological priming for DTH to the T-hapten. Mice were treated with cyclophosphamide (200 mg/kg) and immunized two days later with varying concentrations of the T-3a. Seven days later all groups of mice were footpad-challenged with 10 μg of a preparation of T-disaccharide bound to *C. thermohydrosulfuricum* (T-L111) S-layer. Footpad swelling was measured 24 h later. The increase in footpad thickness is expressed in mm $\times 10^{-1}$.

FIG. 4. Effect of the concentration of T-disaccharide-linked to *C. thermohydrosulfuricum* (T-L111) on the induction of the DTH response to the T-hapten. Mice were treated with cyclophosphamide (200 mg/kg) and immunized two days later with 10 μg of a preparation containing T-disaccharide bound to *B. stearothermophilus* (T-3a) S-layers. Seven days later groups of mice were footpad-challenged with varying amounts of T-disaccharide bound to L111 S-Layers. Footpad swelling was measured 24 h later. The increase in footpad thickness is expressed in mm $\times 10^{-1}$.

FIG. 5. Groups of mice were treated with cyclophosphamide or not and subsequently sham-immunized or immunized with 10 μg of a preparation of T-disaccharide bound to *B. stearothermophilus* (T-3a) S-Layers, mixed with PBS, DDA or FIA. Seven days later each group of mice were footpad challenged with 10 μg of a preparation of T-disaccharide bound to *C. thermohydrosulfuricum* (T-L111) S-Layers. Footpad swelling was measured 24 h later. The increase in footpad thickness is expressed in mm $\times 10^{-1}$.

Figure 6:
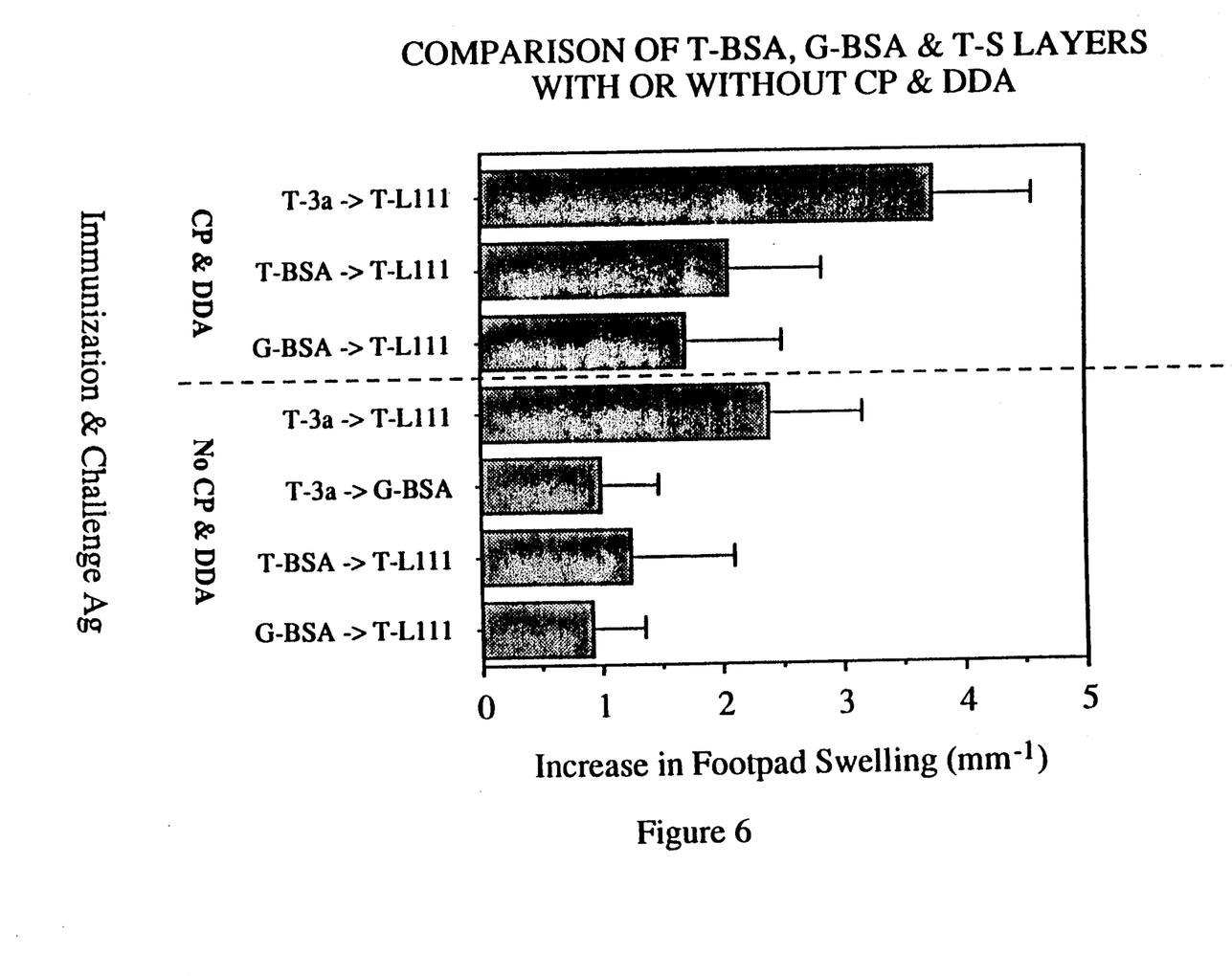
FIG. 6 shows a comparison of the delayed-type-hypersensitivity reaction (DTH) as a result of immunization with hapten linked to a carrier of the invention with hapten linked to BSA.

FIG. 6. Groups of 10 mice were treated, or not, with cyclophosphamide and subsequently immunized with 10 μg of a preparation of T-disaccharide bound to *B. stearothermophilus* (T-3a) S-Layers, 10 μg T-disaccharide bound to bovine serum albumin (BSA) or 10 μg of the 8-methylony carbonyal octanol space arm (that attaches the T-disaccharide to the S-Layer) bound to BSA (G-BSA) with or without DDA. Seven days later each group of mice were footpad challenged with 10 μg of a preparation of T-disaccharide bound to *C. thermohydrosulfuricum* (T-L111) S-Layers or 10 μg of the 8-methylony carbonyal actonal space arm bound to BSA. Footpad swelling was measured 24 h later. The increase in footpad thickness is expressed in mm $\times 10^{-1}$ plus 1 Standard deviation.

FIG. 7. Transfer of the lymphocytes mediating DTH response against the T-disaccharide. A group of 10 mice were pretreated with cyclophosphamide and subsequently immunized with 10 μg of a preparation of T-disaccharide-3a-S-Layer (T-3a). Seven days later mice were sacrificed and draining lymphnodes and spleens were isolated. Purified lymphocytes were then isolated and cultured in RPMI 1640 supplemented with 2% Ultroser Hy, and 1% penicillin and streptomycin. The T-disaccharide-3a primed lymphocytes were bulk stimulated with either PBS, L111 S-Layers, or T-disaccharide-L111-S-Layer conjugates (T-L111). Four days later the lymphocytes were collected and washed in PBS. Primed lymphocytes stimulated with T-disaccharide-L111 were then divided into 4 groups and sham treated or treated with monoclonal antibodies L3T4, (specific for helper T-cells), Ly 2.2 (specific for suppressor T-cells) and Thy 1.2 (specific for all T-cells). The 4 groups cells were then treated with complement and then washed and counted. The primed cells ($5 \times 10^5$) were then mixed with either PBS or T-disaccharide 2051 S-Layer (T-2051) and then injected into naive mice. Footpad swelling was measured 24 h later. The increase in footpad thickness is expressed in mm $\times 10^{-1}$.

We claim:

1. A pharmaceutical composition which comprises a protein or glycoprotein carrier which is a two-dimensional crystalline array comprising purified ordered surface layers (S-layers) layers of microbial cell walls, said carrier coupled with an epitope-bearing moiety.

2. The composition of claim 1 wherein said S-layers are fixed using at least one cross-linker.

3. The composition of claim 1 wherein said epitope-bearing moiety is a carbohydrate.

4. The composition of claim 4 wherein said carbohydrate is selected from the group consisting of betaGal(1-3)alphaGalNAc;
alphaFuc(1-2)betaGal(1-4)[alphaFuc(1-3)]betaGlcNAc;
alphaNANA(2-3)betaGal(1-3)[alphaFuc(1-4)]betaGlcNAc;
alphaNANA(2-3)betaGal(1-3)[alphaFuc(1-3)](1-4)betaGlcNAc; and
betaGal(1-4)[alphaFuc(1-3)]betaGlcNAc.

5. The composition of claim 1 wherein said S-layer is derived from a bacterium selected from the group consisting of *Clostridium thermohydrosulfuricum, Bacillus stearothermophilus*, and *Bacillus alvei*.

6. A method to prepare an immunogenic composition, which method comprises: coupling an epitope-bearing moiety to a carrier which is a protein or glycoprotein crystalline array, said carrier comprising the ordered S-layers of microbial cell walls.

* * * * *